US009532747B2

(12) United States Patent
LaBelle et al.

(10) Patent No.: US 9,532,747 B2
(45) Date of Patent: Jan. 3, 2017

(54) SYSTEM AND METHOD FOR STRESS SENSING

(71) Applicants: Jeffrey T. LaBelle, Tempe, AZ (US); Jorge Tenorio, Chandler, AZ (US); Kevin Uchimura, Gilbert, AZ (US); Benjamin Cantrill, Phoenix, AZ (US)

(72) Inventors: Jeffrey T. LaBelle, Tempe, AZ (US); Jorge Tenorio, Chandler, AZ (US); Kevin Uchimura, Gilbert, AZ (US); Benjamin Cantrill, Phoenix, AZ (US)

(73) Assignee: Arizona Board of Regents, a body of corporate of the State of Arizona, Scottsdale, AZ (US)

( * ) Notice: Subject to any disclaimer, the term of this patent is extended or adjusted under 35 U.S.C. 154(b) by 0 days.

(21) Appl. No.: 14/419,133

(22) PCT Filed: Jul. 31, 2013

(86) PCT No.: PCT/US2013/053071
§ 371 (c)(1),
(2) Date: Feb. 2, 2015

(87) PCT Pub. No.: WO2014/022586
PCT Pub. Date: Feb. 6, 2014

(65) Prior Publication Data
US 2015/0238140 A1 Aug. 27, 2015

Related U.S. Application Data

(60) Provisional application No. 61/679,502, filed on Aug. 3, 2012.

(51) Int. Cl.
*A61B 5/01* (2006.01)
*A61B 5/08* (2006.01)
(Continued)

(52) U.S. Cl.
CPC .......... *A61B 5/4884* (2013.01); *A61B 5/0002* (2013.01); *A61B 5/01* (2013.01); *A61B 5/024* (2013.01);
(Continued)

(58) Field of Classification Search
CPC .............................. A61B 5/0428; A61B 5/721
(Continued)

(56) References Cited

U.S. PATENT DOCUMENTS 6,494,829 B1  12/2002  New et al.
8,214,007 B2   7/2012  Baker et al.
(Continued)

OTHER PUBLICATIONS

International Search Report and Written Opinion for related application No. PCT/US2013/053071, Nov. 20, 2013.

*Primary Examiner* — Carl H Layno
*Assistant Examiner* — Jon Eric C Morales
(74) *Attorney, Agent, or Firm* — Quarles & Brady LLP

(57) ABSTRACT

A system for non-invasively monitoring a stress level of a subject is presented. A sensor is configured to monitor an attribute of the subject. A housing is configured to removably attach to the subject, the housing includes a processor in communication with the sensor, the processor is configured to retrieve data from the sensor, and use the data retrieved from the sensor to determine a stress level of the subject.

6 Claims, 7 Drawing Sheets

(51) Int. Cl.
*A61B 5/024* (2006.01)
*A61B 5/00* (2006.01)
*A61B 5/16* (2006.01)
*A61B 5/0488* (2006.01)

(52) U.S. Cl.
CPC ......... *A61B 5/02405* (2013.01); *A61B 5/0816* (2013.01); *A61B 5/16* (2013.01); *A61B 5/681* (2013.01); *A61B 5/7278* (2013.01); *A61B 5/0488* (2013.01); *A61B 5/6824* (2013.01); *A61B 2562/164* (2013.01)

(58) Field of Classification Search
USPC .................................................. 600/300, 509
See application file for complete search history.

(56) References Cited

U.S. PATENT DOCUMENTS

| | | | |
|---|---|---|---|
| 2008/0146890 A1 | 6/2008 | LeBoeuf et al. | |
| 2008/0183090 A1* | 7/2008 | Farringdon | A61B 5/0428 600/509 |
| 2011/0214280 A1 | 9/2011 | Kiani | |

* cited by examiner

SYSTEM AND METHOD FOR STRESS SENSING

CROSS-REFERENCE TO RELATED APPLICATIONS

This application claims priority to U.S. Provisional Patent Application No. 61/679,502 filed on Aug. 3, 2012 and entitled "SYSTEM AND METHOD FOR STRESS SENSING."

BACKGROUND OF THE INVENTION

Chronic stress is detrimental to one's health and can lead to many stress-based or stress-induced diseases. The difficulty in managing stress, from both a clinical and societal perspective, is that stress is difficult to quantify—what is stressful for one person may not be for another. Some stress is essential in life and, in healthy amounts, stress can provide motivation to accomplish goals. Sometimes stress is necessary in order for the body to protect itself and to overcome obstacles. But the long-term effects of prolonged physiological and psychological stress can and will cause the body harm.

A number of different techniques exist for determining the stress level of a subject. Example techniques include, for example, heart rate variability (HRV) analysis, biological impedance analysis (BIA), body surface temperature analysis, body core temperature analysis, muscle twitch analysis, and respiratory rate analysis.

Heart rate variability (HRV), for example, is a measure of the fluctuations of the heartbeat. Even the beats of a resting heart rate are not perfectly routine or rhythmic, with some variability in the heartbeat frequency. Study of this heartbeat variability is a non-invasive technique providing information about both parasympathetic and sympathetic activity within a subject. Although there are limitations, simple time and frequency domain techniques are commonly used to give quantitative measures allowing implications about stress to be understood.

BIA relies upon skin impedance to analyze a subject's stress. Body surface and body core temperature analysis rely upon body temperatures to analyze a subject's stress. Muscle twitch analysis involves detecting muscle twitch within a subject to analyze stress and respiratory rate analysis looks at a subject's respiratory rate to determine stress.

Although these techniques provide some methods for analyzing a subject's stress, no devices exist that automatically use these techniques to determine a user's stress.

DETAILED DESCRIPTION OF THE INVENTION

Figure 1:
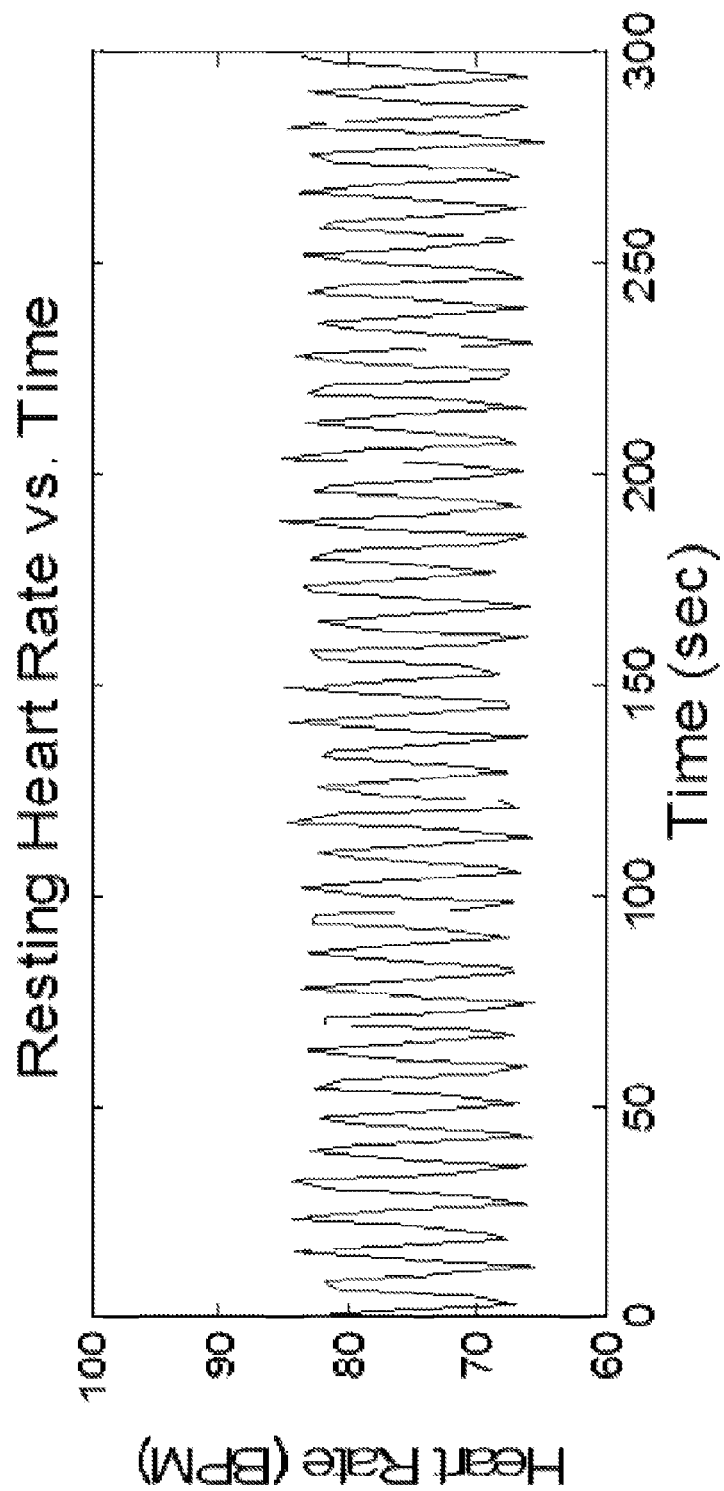
FIG. 1 is a graph showing variability in heart rate of a resting heart over time.

The present disclosure relates to systems and methods for using non-invasive techniques to determine a stress level within a subject. In one implementation, the system includes a device arranged to use a number of non-invasive techniques for investigating a stress level of a subject. The device can be useful to indicate to a subject a level of stress within the subject using a number of different display modes, thereby provide feedback to the subject. The device can collect data continuously over an extended time period to provide a dataset useful for trending analysis of the subject's stress levels. In one implementation, the device allows a subject to input his or her personal statistics such as age, height, and weight to provide individualized and more accurate data analysis.

By using multiple quantitative methods for stress analysis within a single device, a more accurate analysis of stress in a subject can be achieved. Use of a device that incorporates multiple analytical techniques allows for the analysis of the onset of stress in a subject, and the effects of stress after the stress occurs. Not only would the device be useful in measuring stress, but the device would also be useful in measuring other vital health signs. The quantification of stress could be used in a variety of settings to assess the health of subjects during different activities.

The present system may be used in a number of different settings or applications, including use in critical care transport, and use by first responders, fire fighters, and military personnel. In the hospital setting, the system can also be used to monitor stress levels in critical care patients, for example.

When used by first responders, the system can assist in monitoring and providing patient stabilization and management. The system could be used to assess a patient's initial medical condition, for example. Then, based on a level of stress, responders can better assess the patient's immediate medical needs. In this situation, perhaps a rescue operation after a natural disaster, the system could also be worn by the first responder, allowing command and control operations to monitor rescuers as well as survivors found. In critical care transport, the system could be used to monitor stress levels in a patient to determine proper medical procedure both while in transport and upon arrival at a medical facility. Stress monitoring during transport could be used to assess the progression of the patient's medical condition, for example. The system can also be used for patient monitoring to better assess the stability of a patient's health during an operation or treatment. The system could also be used to monitor and collect data from the patient before and after treatment. The system could also be used to monitor the stress levels of first responders or military personal to perform on-going health assessments.

The present system can use a number of different non-invasive techniques for determining a stress level within the subject. Example non-invasive stress monitoring techniques include heart rate variability (HRV) analysis, biological impedance analysis (BIA), Galvanic Skin Resistance (GSR), body surface temperature analysis, body core temperature analysis, muscle twitch analysis, and respiratory rate analysis.

A first non-invasive stress monitoring technique includes HRV analysis. The interval between heartbeats continuously fluctuates due to sympathetic and parasympathetic nerve activity. It is ideal for changes in heart rate to be reflected by a smooth, sine wave-like pattern as opposed to abrupt changes. Heart rate variability (HRV) analysis is a non-invasive technique generally implemented by monitoring the interval between successive peaks of the QRS complex (the R-R interval) of an EKG signal and can give implications about a subject's stress.

In a subject, instantaneous heart rate is regulated by the interplay between multiple physiologic mechanisms. In healthy subjects, the sinoatrial (SA) node in the right atrium initiates each beat of the heart. Action potentials are generated by the SA node's autorhythmicity but are modulated by many factors that add variability to the heart rate signal. In heart rate variability analysis, the RR interval is defined as the time between QRS peaks in the EKG signal. The RR interval can also be referred to as the NN interval because the interval can be thought of as the normal-to-normal interval. In many research applications, this data is recorded and called the interbeat interval (IBI). The magnitude of variability in the beat-to-beat changes of the RR interval are generally a sign of sound cardiovascular health. A more healthy state is also characterized by a heart rhythm pattern that changes smoothly, resembling a sine-wave. Abrupt changes are indicative of a less ordered state and can indicate stress.

Figure 2:
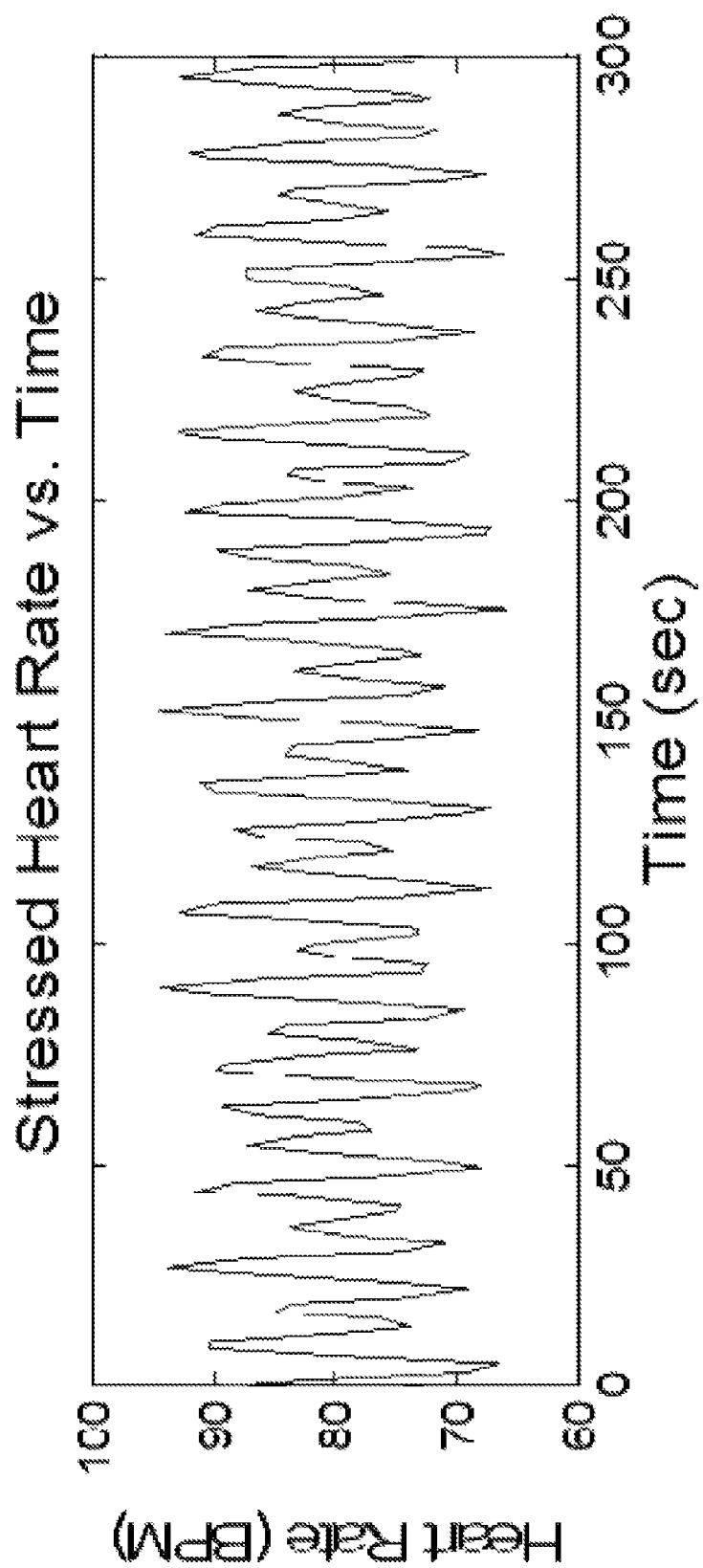
FIG. 2 is a graph showing variability in heart rate in a subject experiencing physical stress, such as exercise.

FIG. 1 is a graph showing variability in heart rate of a resting heart over time. As illustrated, heart rate is not a static value as it continually fluctuates. In the example shown in FIG. 1, though, the changes are relatively smooth and the amplitude is fairly consistent. FIG. 2, in contrast, shows an example of how the heart rate can change with stress. The changes in heart rate are more abrupt and much less rhythmic than the resting example shown in FIG. 1. The mean heart rate has also increased. If data is recorded after a subject exercises, the heart rate will initially be much higher than resting and slowly returned to baseline as the subject recovers.

The most commonly used HRV measures fall into categories of time domain and frequency domain measures. A summary can be seen in Table 1, below. Time domain measures derived directly from the lengths of IBIs are the mean IBI and the standard deviation of NN intervals. The parameters that are based on the difference between consecutive IBI lengths are NN50, pNN50, and RMSSD. NN50 is the number of successive NN interval differences greater than 50 ms. pNN50 refers to the percentage of NN50 to the total number of NN intervals. A normal value is between 5 and 10 percent. Lastly, RMSSD is the root mean square of differences between consecutive NN intervals. A RMSSD for a healthy person is expected to be around 15 to 40 ms in many cases. However, the typical values given are not accepted standards and significant variation can be seen in different populations.

TABLE 1

| Time Domain | Frequency Domain |
| --- | --- |
| SDNN—Standard deviation of NN intervals | Total Power—Total spectral power of all NN intervals up to 0.4 Hz |
| SDANN—Standard deviation of the average NN intervals | VLF—Total spectral power of all NN intervals in the VLF range (0.033-0.04 Hz) |
| RMSSD—Square root of the mean squared difference of successive NNs | LF—Total spectral power of all NN intervals in the LF range (0.04-0.15 Hz) |
| NN50—Number of pairs of successive NNs that differ by more than 50 ms | HF—Total spectral power of all NN intervals in the HF range (0.15-0.4 Hz) |
| pNN50—Proportion of NN50/total # NNs | LF/HF—Ratio of low to high frequency power |

The remaining measurement techniques in Table 1 require frequency domain analysis. Power spectral density (PSD) analysis provides the basic information of how power distributes as a function of frequency. The frequency domain methods are thought to show the parasympathetic and sympathetic influences in a more clinically meaningful manner. The heart rate variability frequency spectrum is broken up into three main ranges. The very low frequency range (VLF) is from 0.033-0.04 Hz, the low frequency range (LF) is from 0.04-0.15 Hz, and the high frequency range (HF) is from 0.15-0.4 Hz.

In general, the LF range corresponds to sympathetic activity and the HF range corresponds to parasympathetic activity. However, a closer examination shows that other mechanisms and feedback loops are also at work, especially in the LF range. The LF range may be related to both sympathetic and parasympathetic modulation. Given that relationship, a common measure is to calculate the power in the LF and HF ranges. The ratio of LF to HF power can then be used as a metric of parasympathetic and sympathetic balance. The VLF range is normally not considered in short-term recordings. However, it can be important to record so that the total power in the heart rate variability spectrum can be known.

The study of heart rate variability has many implications. It is feasible that its use can aid in diagnostic and preventive healthcare. HRV provides insights about controlling the heart rate and can help predict cardiovascular risk in both health and disease. Low values of heart rate variability are a predictive marker for diabetic autonomic neuropathy, hypertension, myocardial infarction, and heart failure. Most HRV measures also show an age-related decline. However, it is important to realize that many variables likely have an effect including activity levels, breathing, gender, and sleep.

When monitoring HRV, the present device records EKG signals from a subject, performs a Fourier transform of the real-time data and uses a power spectrum density plot to establish frequency effects over a given time interval (say every 60 seconds of data, though other periods may be used) that then is correlated by an HRV algorithm into a single data point (every 60 seconds) and is updated continuously, as long as the device is worn.

Another non-invasive method of investigating stress in a subject is biological impedance analysis (BIA) and/or Galvanic Skin Resistance (GSR). Emotional stress causes perspiration release from apocrine glands, and physical stress causes perspiration release from eccrine glands. By measuring changes in total body water (TBW) due to water loss through sweat, hydration level can be used as a measure of stress. Changes in hydration level can be measured using BIA or GSR, which uses a small current to receive a voltage to assess resistance in the body due to TBW. This resistance can be monitored by a resistivity sensor, as described below.

Figure 3:
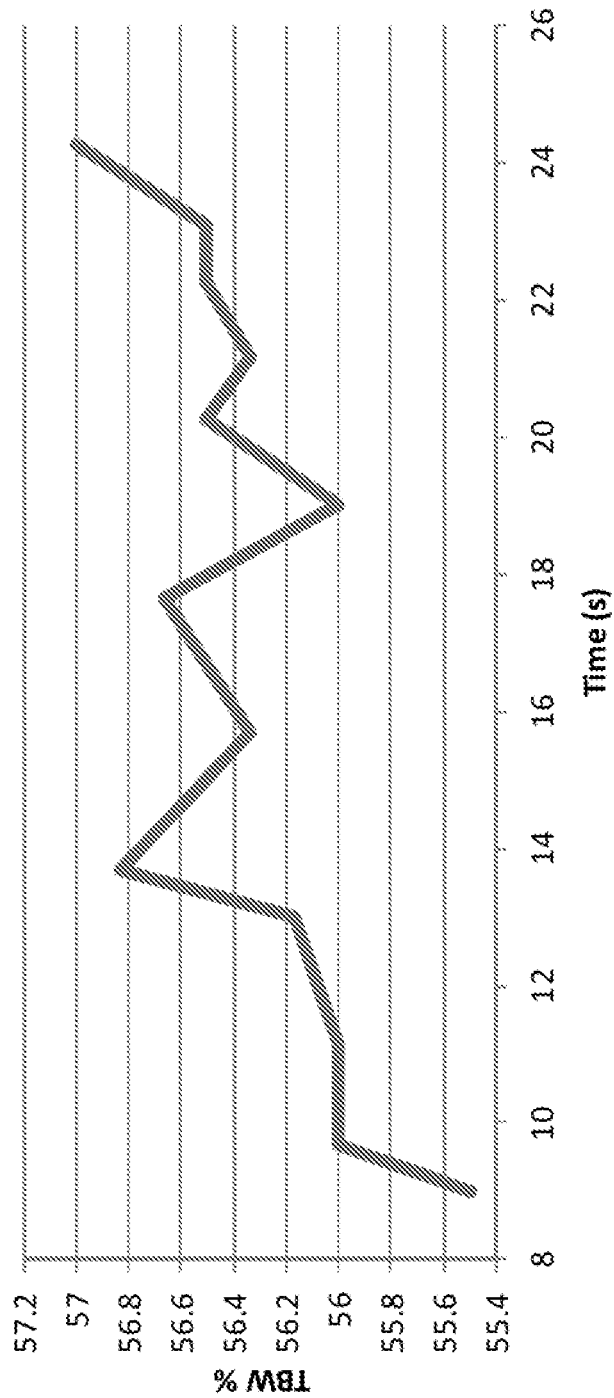
FIG. 3 is a graph showing an idealized representation of changes in total body water percent in a subject versus time as the person is hydrated while under physical stress, such as exercise.

Using a linear regression, total body water percent of a subject can be accurately estimated. In the present system, the subject's height, weight, age, and gender are entered using an appropriate user interface on the device and the resistance would be obtained using BIA or GSR. In one example, total body water is equal to $0.372(S^2 \div R)+3.05(Sex)+0.142(W)-0.069(age)$ where S=Height of the subject in centimeters, R is the measured resistance, W is the subject's weight in Kg, and Sex has a value of 1 for males and 0 for females. FIG. 3 is a graph showing an idealized representation of what the output would be as TBW percent changes in seconds.

When a person undergoes stress, the electrical behavior of their body changes, namely in sweat, hydration, among others. These subtle changes can be monitored using BIA or GSR as well as inducing a phase angle measurement to differentiate between resistance and reactance from the measured total resistance.

Another non-invasive stress sensing technique is body surface temperature analysis. Events that take place in the brain can influence the surface temperature of the skin of a subject. Both physical and cognitive stress can cause vasodilation to occur to increase blood flow to the skin. Peripheral vasodilation along with other responses cools the surface of the body and reduces blood temperature. By measuring changes in surface temperature, therefore, it is possible to determine a person's level of stress.

Thermistors can be placed into a voltage divider circuit and with a small signal placed onto the thermistor, the change in voltage measured across the load resistor can be correlated to surface body temperature. As a person exercises or undergoes stress, the change in stress causes a change in blood flow that changes surface temperature.

Similarly, the subject's core body temperature can be used to sense a level of stress within a subject. The hypothalamus is responsible for thermoregulation and adapting to changing temperatures. During physical stress, core body temperature will rise and can be used as a measure of stress. To implement this approach, a temperature sensor can be swallowed by a subject to monitor core temperature and the data can be collected and output by an external device. By monitoring changes in core temperature, physical stress can be better assessed.

As with the surface temperature, under stress, the body will consume glucose and other energy storage molecules leading to a core temperature change due to a stressed induced metabolic consumption. The core body temperature is slightly more invasive than surface but can be a higher degree accurate.

Another non-invasive stress sensing technique involves the monitoring of a subject's muscle twitches. During moments of emotional and physical stress, muscles will contract such as those on the face or arms. By measuring the magnitude and frequency of muscle contractions during stress, muscle twitches can be used as a measure of stress. Devices used to evaluate muscle contraction use the electrical signals at the neuromuscular junction to measure stimulus responses.

Figure 4:
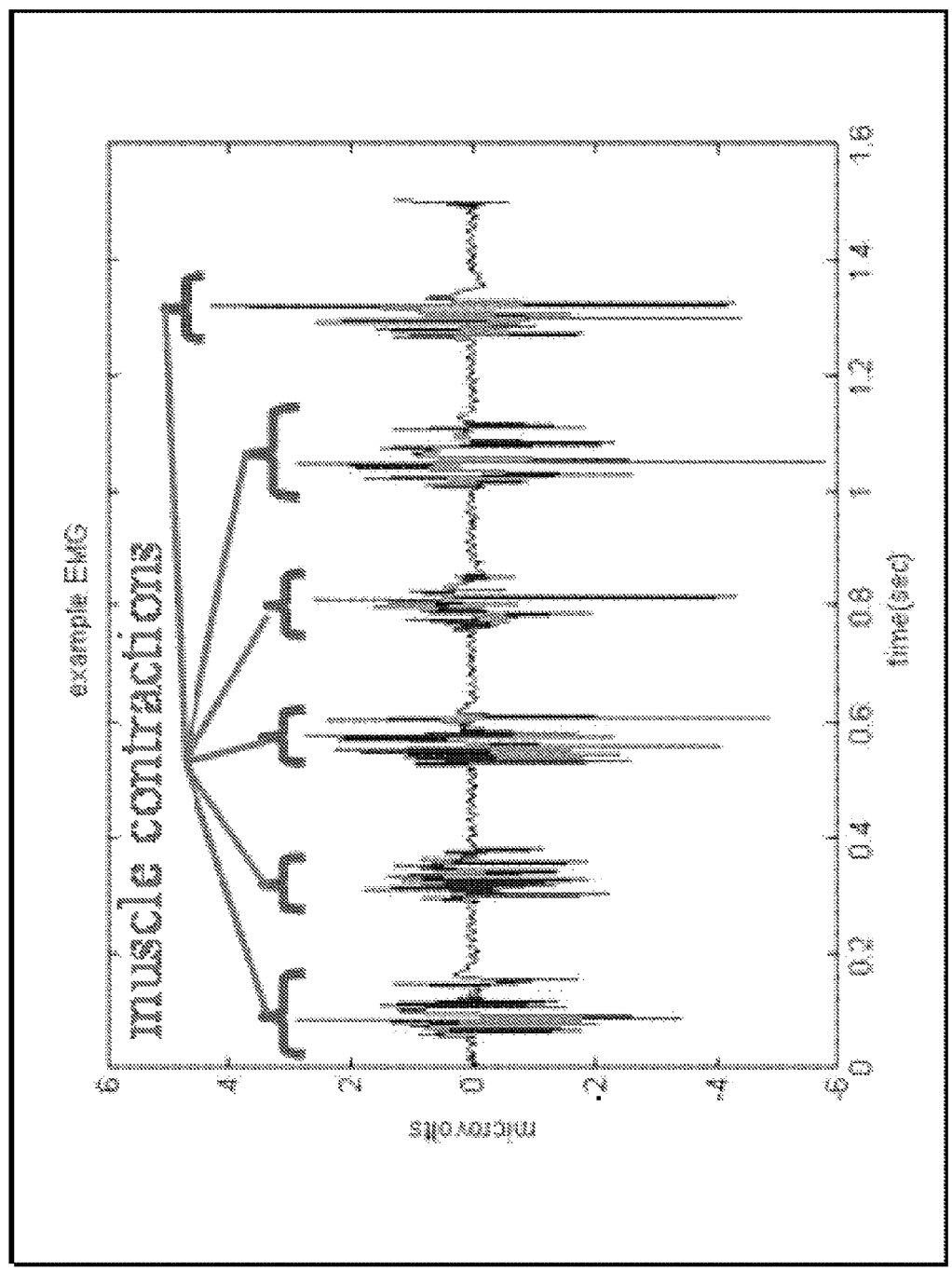
FIG. 4 is a graph showing results of an EMG scan that captures groups of muscle twitch signals in a subject while performing physical exercise.

Electromyography is a technique that can be used to monitor muscle twitching in a subject, which, in turn, can be used to determine a level of stress within that subject. FIG. 4, for example, is a graph showing an EMG scan that captures groups of muscle twitch signals in a subject.

As a person is under stress, muscle twitches, as compared to baseline, can increase or completely develop in areas of nonactivity. By measuring EMG and performing a frequency analysis on the occurrence (as well as location) of twitches a correlation change be made to stress levels.

Another non-invasive stress sensing technique involves the monitoring of respiratory rate within a subject. Under stress, a subject's breathing pattern changes effecting gas exchange in the lungs. In some cases, hyperventilation occurs and prolongs others symptoms of stress. Changes in breathing patterns occur when activated by the sympathetic nervous system during stress. By monitoring changes in lung volume and breathing patterns, breathing rate can be used to evaluate a person's level of stress.

Figure 5:
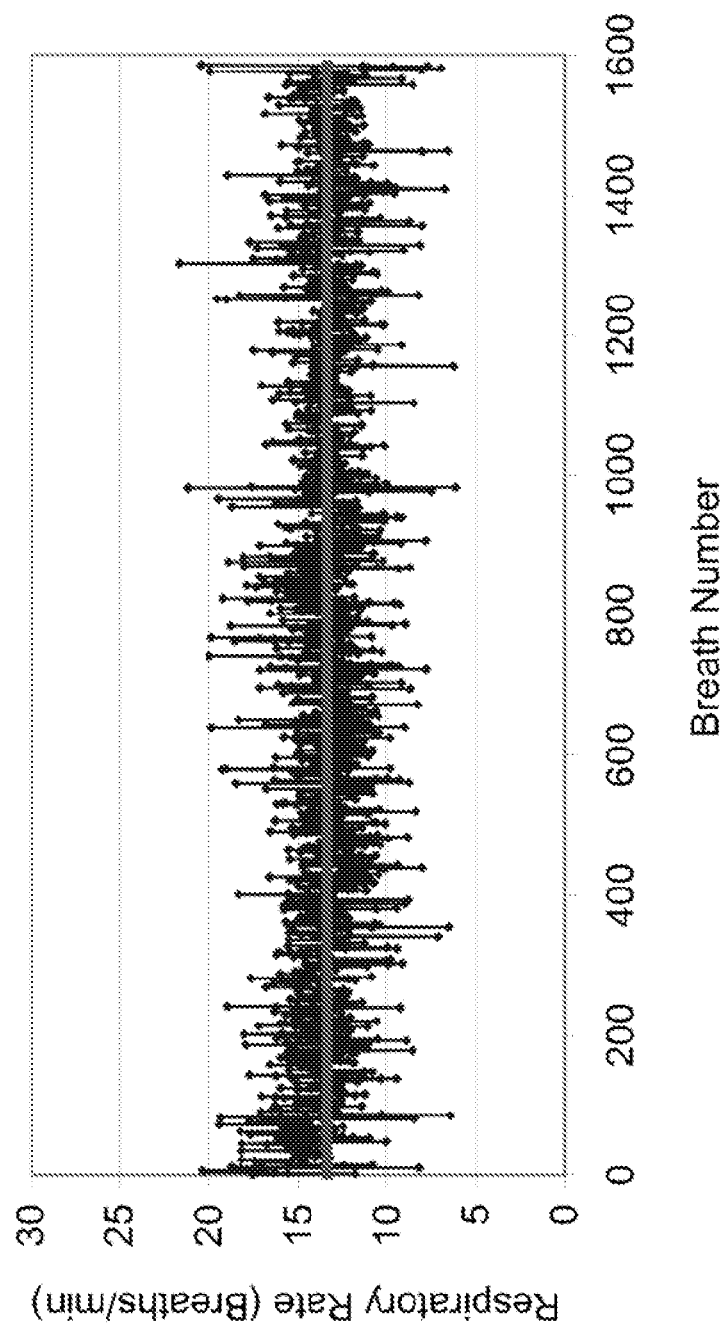
FIG. 5 is a graph showing an output of respiratory rate over a number of breaths for a monitored subject at rest.

When using respiratory rate to monitor stress, data can be collected to observe changes in breathing patterns to indicate an initiation into a state of stress or relaxation. FIG. 5, for example, is a graph showing an output of respiratory rate over a number of breaths for a monitored subject. A device incorporating this tested method can be used as a supplementary method to better evaluate stress variations along with other methods.

Under stressful situations, changes in breathing or respiratory rates can be made off baseline. By monitoring the respiratory rate at rest for an individual, then correlations between rest and while performing stressful or extreme exercise can be made.

The present system provides a wearable device that can utilize a number of non-invasive stress monitoring techniques, such as those described above, to monitor a stress level with a subject. The device can use, for example, one or more of heart rate variability (HRV) analysis, BIA, GSR, body surface temperature analysis, body core temperature analysis, muscle twitch analysis, and/or respiratory rate analysis to determine a stress level of the wearer.

Figure 6:
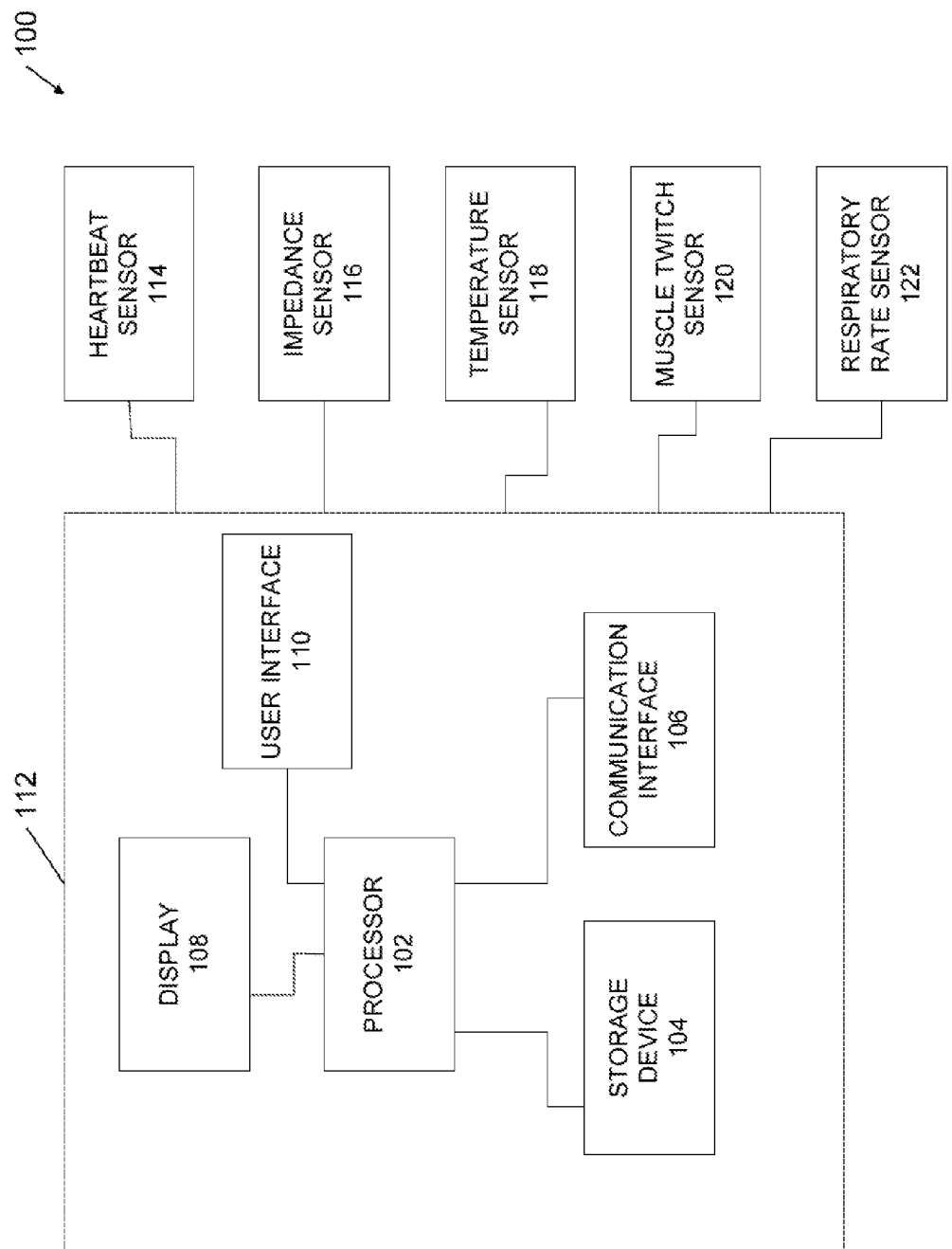
FIG. 6 is a block diagram showing the functional components of a device for monitoring a user's stress level.

FIG. 6 is a block diagram showing the functional components of device 100 for monitoring a wearer's stress level. Device 100 includes a wearable housing 112, described below. Components within wearable housing 112 are in communication with a number of sensors (e.g., sensors 114, 116, 118, 120, and 122). To use the device, the user first mounts housing 112 to his or her person. Then, one or more of the sensors are mounted to the user so as to be able to capture data from the subject's body. The sensors may include skin mounted sensors (e.g., for measuring skin temperature, resistivity, or muscle twitch), or swallowed sensors (e.g., to measure core temperature). After the sensors are mounted, the device collects data from the sensors and then analyzes that data to determine a level of stress within the user. The data analysis techniques will vary based upon the type of data collected from the sensor and the particular form of non-invasive stress monitoring technique being implemented.

In one implementation, housing 112 of device 100 is manufactured by fabricating a number of electronic components and interconnecting circuits over a flexible substrate. The flexible substrate can then be mount to the subject's body, perhaps using an adhesive, and allow for the subject's wearing of the housing 112. For example, device 100 may be manufactured in the form of a "band-aid" that can be applied to the subject's skin. In one implementation, device 100 may be fabricated by screen printing conductive paste (e.g., silver-chloride (Ag/AgCl)) over a flexible substrate, such as mylar backing. In other implementations, device 100 may be formed over a polyimide film (e.g., KAPTON), which allows for the fabrication of flexible components. In that case, the device 100 may be fabricated using a number of known photolithography procedures, such as forming a resist coating over the film, applying artwork and ultraviolet light, applying acetone to expose the copper or other conductive material of the film, applying etchant, and developing to remove exposed photoresist). Photoresist may be applied to the film using spin coating (in the case that the photoresist is a liquid), or using a dry film photoresist that can be rolled on to the film rather than spin-coated.

Device 100 includes processor 102. Processor 102 is configured to communicate with and receive data from a number of sensors in communication with processor 102, as described below. In one implementation, processor 102 communicates with the sensors using communication interface 106. Communication interface 106 may allow for combinations of wired and/or wireless communications with one or more sensors. Example wireless communication systems include Bluetooth, systems based upon the 802.11 standard, and others.

Processor 102 is in communication with storage device 104. Storage device 104 includes an electronic storage medium such as a disk drive, solid-state memory device, and/or the like. When collecting sensor data over an extended period of time, for example, processor 102 can store data in storage device 104 for later retrieval and analysis. Additionally, storage device 104 may store a number of electronic instructions that are executed by processor 102 to provide the functionality of device 100.

In one implementation, device 100 can communicate the data captured from the connected sensor to external computing systems, such as a laptop or personal computer. The data can be communicated using communication interface 106 using either a wired or a wireless communication path.

Processor 102 is in communication with display 108 and can use display 108 to display a number of different outputs that are useful for a user. Display 108 may include an organic light emitting diode (OLED) screen, liquid crystal display (LCD) screen, flexible OLED screen, or other suitable display systems. Processor 102 is also in communication with one or more user interface device 110. User interface 110 device may include a keyboard, touch screen, or other user interface allowing the user to provide input that is captured by processor 102. A user, for example, can use user interface 110 to provide device 100 with an indication of the user's height, weight, age, and sex, for example. User interface device 100 can also be used to instruct processor 102 as to which particular information to display using display 108.

Various levels of data presentation are possible. A simple green-red LED level indicator can be envisioned whereby the user can see if their stress levels are in the red (bad) or moving down a scale to ultimately a green (healthy) level. For more clinical use, the actual HR, HRV, RR, BIA, GSR, ST and CT numbers (and respective units) can be given, over time.

Processor 102, storage device 104, communication interface 106, display 108, and user interface 110 are housed and at least partially contained within housing 112. Housing 112 provides a protective enclosure to the components of device 100 and is configured to be easily carried or worn by an individual. For example, housing 112 may be connected to a strap system that allows the housing to worn by an individual. Similarly, housing 112 may be shaped to easily fit within a user's pocket or bag. Housing 112 includes an opening or transparent portion to expose at least a portion of display 108 for viewing by a user.

Accordingly, housing 112 is configured to be portable and durable. In various implementations, housing 112 may also be configured to be waterproof. Housing 112 generally includes a power source to provide energy to the components connected to housing 112. The power source can include, for example, flexible batteries or other battery systems that provide energy for a suitable period of time.

Processor 102 may be programmed (via instructions contained within storage device 104) to capture data from a number of different sensors for performing non-invasive stress analysis of a subject.

For example, when device 100 is used with heartbeat sensor 114, processor 102 can communicate with heartbeat sensor 114 through communication interface 106 (either wired or wireless) to capture data therefrom. Heartbeat sensor 114 may include EKG surface leads like a RAM electrode, pulsometer, etc. Heartbeat sensor 114 is configured to detect heartbeats within the user. After data is captured from heartbeat sensor 114, processor 102 can analyze the data to determine an amount of heart rate variability using the techniques described above. That heart rate variability can then be used to determine a stress level of the subject.

Similarly, device 100 may be used with impedance sensor 116. Impedance sensor 116 includes a skin-mounted sensor configured to detect an impedance or resistance of the user's skin. Processor 102 can communicate with impedance sensor 116 through communication interface 106 (either wired or wireless) to capture data therefrom. Impedance sensor 116 may include RAM electrodes. After data is captured from impedance sensor 116, processor 102 can analyze the data using the biological impedance analysis technique described above to determine a stress level of the subject. In some cases, the biological impedance analysis uses data provided by the user to device 100 through user interface 110 identifying various characteristics of the user such as height, weight, sex, and age, for example.

Device 100 may be used with temperature sensor 118. Temperature sensor 118 may include one or more temperature sensors configured to measure a temperature of user's skin and/or the user's core. When measuring the temperature of the user's skin, temperature sensor 118 may include RTD, thermistors, thermocouples, etc. When measuring the temperature of the user's core, temperature sensor 118 may include RTD, thermistors, thermocouples, etc. Processor 102 can communicate with temperature sensor 118 through communication interface 106 (either wired or wireless) to capture data therefrom. After data is captured from temperature sensor 118, processor 102 can analyze the temperature data using the temperature (core or skin) analysis techniques described above to determine a stress level of the subject.

Device 100 may be used with muscle twitch sensor 120. Muscle twitch sensor 120 includes a sensor that can be connected to the user's skin and configured to detect muscle twitches in regions proximate the sensor. In various implementations, muscle twitch sensor 120 may include RAM electrodes. Processor 102 can communicate with muscle twitch sensor 120 through communication interface 106 (either wired or wireless) to capture data therefrom. After data is captured from muscle twitch sensor 120, processor 102 can analyze the muscle twitch data using the muscle twitch analysis techniques described above to determine a stress level of the subject.

Device 100 may be used with respiratory rate sensor 122. Respiratory rate sensor 122 includes a sensor that is configured to detect a rate of the user's breathing. In various implementations, respiratory rate sensor 122 may include flexible resistors, acoustic sensors, piezoelectric sensors, etc. Processor 102 can communicate with respiratory rate sensor 122 through communication interface 106 (either wired or wireless) to capture data therefrom. After data is captured from respiratory rate sensor 122, processor 102 can analyze the respiratory rate data using the respiratory rate analysis techniques described above to determine a stress level of the subject.

Depending upon the system implementation, device 100 may include any combination of sensors 114, 116, 118, 120, and 122. For example, processor 102 may be configured to use communication interface 106 to attempt to communicate with a number of potential sensor systems. After attempting to communicate with the sensors, processor 102 can identify a number of sensors that are responsive and capturing data (i.e., sensors that are in use). Then, the processor can use data captured from those sensors to perform stress analysis. As additional sensors are added to the system (or, conversely, removed from the system), the processor uses data captured from the available sensors to perform stress analysis.

Figure 7:
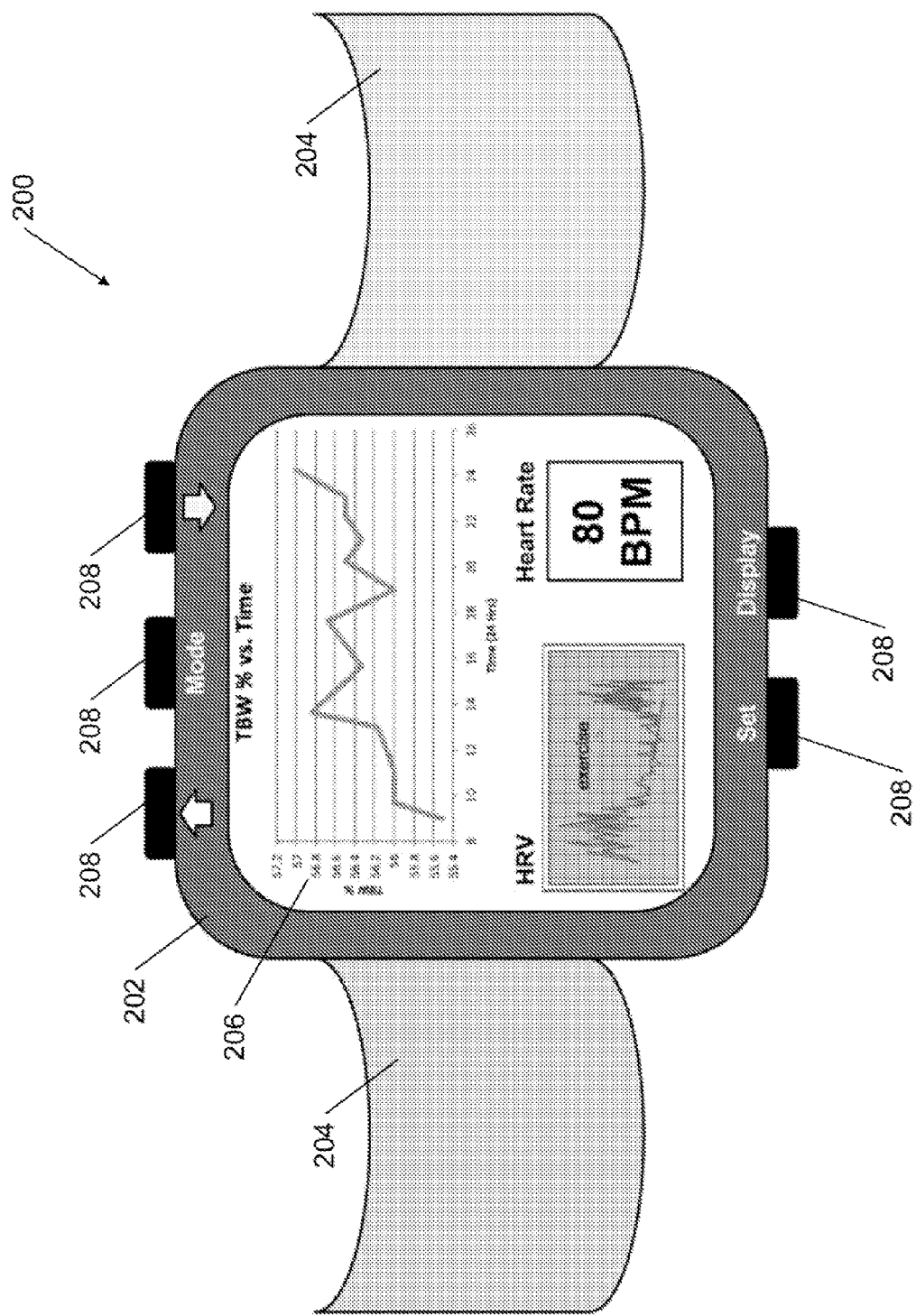
FIG. 7 is an illustration showing an example wearable and integrated device for monitoring stress of a user configured in accordance with the present disclosure.

FIG. 7 is an illustration showing an example device for monitoring stress of a user configured in accordance with the present disclosure. Device 200 includes housing 202 configured to contain the components of device 200. Housing 200 incorporates a pair of straps 204 configured to attach about the user's wrist. Housing 202 incorporates a display 206 configured to display an output of device 200. Referring to FIG. 7, housing incorporates display 206 for providing information to the user. A number of user interfaces 208 are positioned about housing 202 allowing a user to interact with device 200. User interfaces 208 allow the user to control the information that is displayed on display 206 as well as input information (such as the user's height, weight, age and sex) into device 200. In various other implementations of device 200, a number of different attachment mechanisms may be provide for attaching device 200 to a user. For example, housing 200 may incorporate waist straps, head bands, belt loops, and the like, to allow housing 200 to be easily carried by a user.

The materials and methods described above are not intended to be limited to the embodiments and examples described herein.

The invention claimed is:

1. A device for non-invasively monitoring a stress level of a subject, comprising:
   a housing configured to removably attach to the subject, the housing including:
      a flexible substrate including polyimide film and mylar backing, the flexible substrate being configured to attach to a surface of a skin of the subject,
      a processor mounted to the polyimide film over the flexible substrate, the processor being configured to communicate with a heartbeat sensor, the heartbeat sensor being configured to detect a heartbeat of the subject, the processor being configured to:
      retrieve data from the heartbeat sensor,
      determine, using the data from the heartbeat sensor, a heart rate variability of the subject, and
      use the heart rate variability of the subject to determine a stress level of the subject.

2. The device of claim 1, including an impedance sensor configured to measure an impedance of a skin of the subject and wherein the processor is configured to use the impedance of the skin of the subject to determine the stress level of the subject.

3. The device of claim 1, including a temperature sensor configured to measure a temperature of a skin of the subject and wherein the processor is configured to use the temperature of the skin of the subject to determine the stress level of the subject.

4. The device of claim 1, including a core temperature sensor configured to measure a temperature of a core of the subject and wherein the processor is configured to use the temperature of the core of the subject to determine the stress level of the subject.

5. The device of claim 1, including a respiratory rate sensor configured to measure a respiratory rate of the subject and wherein the processor is configured to use the respiratory rate of the subject to determine the stress level of the subject.

6. The device of claim 1, wherein the processor is configured to communicate with the heartbeat sensor using a wireless communication interface.

* * * * *